United States Patent [19]

Berkowitz et al.

[11] Patent Number: 5,221,664

[45] Date of Patent: Jun. 22, 1993

[54] COMPOSITION AND TREATMENT WITH BIOLOGICALLY ACTIVE PEPTIDES AND TOXIC CATIONS

[75] Inventors: Barry Berkowitz, Ft. Washington; Leonard Jacob, Penn Valley, both of Pa.

[73] Assignee: Magainin Pharmaaceuticals Inc., Plymouth Meeting, Pa.

[21] Appl. No.: 794,828

[22] Filed: Nov. 18, 1991

Related U.S. Application Data

[63] Continuation of Ser. No. 512,345, Apr. 23, 1990, abandoned.

[51] Int. Cl.$^5$ .............. A61K 37/02; C07K 7/10
[52] U.S. Cl. .......................... 514/6; 514/12; 514/13; 514/21; 530/324; 530/325; 530/326; 530/350; 530/842
[58] Field of Search .............. 514/12, 13, 21, 6; 530/324, 325, 326, 842, 350

[56] References Cited

U.S. PATENT DOCUMENTS 4,507,230  3/1985  Tam et al. .............. 530/337
4,962,277  10/1990  Cuervo et al. .......... 514/14

FOREIGN PATENT DOCUMENTS

WO8911290  11/1989  PCT Int'l Appl. .
WO9004407  5/1990   PCT Int'l Appl. .
WO9100869  1/1991   PCT Int'l Appl. .

OTHER PUBLICATIONS

Gibson, et al., "Novel Peptide Fragments Originating from PGLa and the Caerulein and Xenopsin Precursors" from *Xenopus laevis*, *J. Biol. Chem.*, vol. 261, No. 12 (Apr. 25, 1986).

Giovannini, et al. "Biosynthesis and Degradation of Peptides Derived from *Xenopus laevis* Prohormones," *Biochem J.*, vol. 243, pp. 113-120 (1987).

Christensen, et al., *Proc. Nat. Acad. Sci.*, vol. 85, pp. 5072-5076 (Jul. 1988).

*Primary Examiner*—Lester L. Lee
*Assistant Examiner*—Carol Salata
*Attorney, Agent, or Firm*—Elliot M. Olstein; Raymond J. Lillie

[57] ABSTRACT

A composition comprising a biologically active amphiphilic ion channel-forming peptide or ion channel forming protein and a toxic cation, such as a silver cation. Such compositions may be employed as pharmaceuticals, particularly for the treatment and prevention of eye infections.

94 Claims, No Drawings

COMPOSITION AND TREATMENT WITH BIOLOGICALLY ACTIVE PEPTIDES AND TOXIC CATIONS

This application is a continuation of Ser. No. 512,345, filed Apr. 23, 1990, and now abandoned.

This invention relates to biologically active peptides and proteins, and more particularly to compositions and uses involving biologically active peptides or proteins and toxic cations, in particular silver cations. In particular, such compositions may be employed in preventing and/or treating ocular infections.

Silver-containing compositions, such as silver nitrate, have been used for preventing and/or treating external ocular infections, such as, for example, the prevention and treatment of ophthalmic gonorrhea. Darrell, et al., *Tr. am. Ophthl. Soc.*, Vol. 82 (1984), 75-91, discloses the use of silver norfloxacin, or silver sulfadiazine, or silver sulfacetamide to treat corneal infections caused by *P. aeruginosa*. These compounds also exhibit significant biological activity against *S. aureus*, as well as the fungi *C. albicans*, and *A. fumigatus*.

In accordance with an aspect of the present invention, there is provided a composition which includes at least one biologically active amphiphilic peptide and/or biologically active protein; and a toxic cation.

In accordance with another aspect of the present invention, there is provided a process wherein there is administered to a host at least one biologically active amphiphilic peptide which is an ion channel-forming peptide and/or a biologically active protein which is an ion channel-forming protein and a toxic cation.

An ion channel-forming peptide or protein or ionophore is a peptide or protein which increases the permeability for ions across a natural or synthetic lipid membrane. B. Christensen et al. PNAS Vol. 85 P. 5072-76 (July, 1988) describes methodology which indicates whether or not a peptide or protein has ion channel-forming properties and is therefore an ionophore. As used herein an ion channel-forming peptide or ion channel forming protein is a peptide or protein which has ion channel-forming properties as determined by the method of Christensen et al.

An amphiphilic peptide is a peptide which includes both hydrophobic and hydrophilic peptide regions.

In accordance with an aspect of the present invention wherein the biologically active peptide or protein and toxic cation are administered to a host, such biologically active peptide or protein and toxic cation may be administered as a single composition or in separate compositions, and the single or separate compositions may include additional materials, actives and/or inactives, in addition to the peptide and/or protein and toxic cation.

The compositions of the present invention thus may be used in the treatment of external burns and to treat and/or prevent skin and burn infections. In particular, the compositions may be used to treat skin and burn infections caused by organisms such as, but not limited to, *P. aeruginosa* and *S. aureus*.

The ion channel-forming peptides employed in the present invention are generally water soluble to a concentration of at least 20 mg/ml at neutral pH in water. In addition, such peptides are non-hemolytic; i.e., they will not rupture blood cells at effective concentrations. In addition, the structure of such peptide provides for flexibility of the peptide molecule. When the peptide is placed in water, it does not assume an amphiphilic structure. When the peptide encounters an oily surface or membrane, the peptide chain folds upon itself into a rod-like structure.

In general, such peptides have at least 16 amino acids, and preferably at least 20 amino acids. In most cases, such peptides do not have in excess of 40 amino acids.

In genera, the toxic cation is employed as part of a suitable compound. Toxic cations which may be employed include, but are not limited to, silver cations, zinc cations, mercury cations, arsenic cations, copper cations, platinum cations, antimony cations, gold cations, thalluim cations, nickel cations, selenium cations, bismuth cations, and cadmium cations.

In a particularly preferred embodiment, the toxic cation is a silver cation, which may be employed as part of a suitable compound. Suitable silver-containing compounds which may be employed include silver nitrate, silver acetate, silver benzoate, silver carbonate, silver iodate, silver iodide, silver lactate, silver laurate, silver oxide, silver palmitate, mild silver proteins, and silver sulfadiazine. It is also preferred that the silver-containing composition be water-soluble. In accordance with one embodiment, the toxic cation may be silver nitrate.

Silver nitrate as a 0.5% solution is used in the treatment of external burns, and silver sufladiazine is also used to treat external burns, but bacterial resistance to the sulfonamides (sulfadiazine) can result. S. Harvey, in Goodman and Gilman, *Pharmacological Basis of Therapeutics*, 7th ed., pgs. 966-967; MacMillan (1985).

In employing both an ion channel-forming biologically active amphiphilic peptide or an ion channel-forming protein, and a toxic cation, whether administered or prepared in a single composition, or in separate compositions, the peptide or protein and the toxic cation, are employed in amounts effective to inhibit and/or prevent and/or destroy the growth of the target cell. In effect, the toxic cation potentiates the action of the peptide or protein, and the peptide or protein potentiates the action of the toxic cation. The term "potentiate," as employed herein, means that the amount of toxic cation is effective to reduce the minimum effective concentration of the peptide or protein for inhibiting growth of a target cell and the amount of peptide or protein is effective to reduce the minimum effective concentration of the toxic cation for inhibiting growth of a target cell.

In general, the peptide or protein is administered topically at a concentration of from 0.05% to 5%.

The toxic cation, in general, is used topically at a concentration of from 0.05% to 2.0%.

The use of a combination of peptide or protein and toxic cation in accordance with the present invention is effective as an antibiotic, and may be employed to inhibit, prevent or destroy the growth or proliferation of microbes, such as bacteria and fungi. Similarly, such compositions may be employed as an anti-viral composition to inhibit, prevent or destroy the growth or proliferation of viruses.

Such compositions may also be used as antifungal agents to inhibit the growth of or destroy fungi.

Such compositions may also be used as anti-parasitic agents to inhibit the growth of or destroy parasites.

The compositions have a broad range of potent antibiotic activity against a plurality of microorganisms, including gram-positive and gram-negative bacteria, fungi, protozoa parasites, and the like. Such compositions may be employed for treating or controlling microbial infection caused by organisms which are sensitive to such compositions. The treatment may comprise administering to a host organism or tissues acceptable to or affiliated with a microbial infection an anti-microbial amount of peptide or protein and toxic cation.

The compositions may also be used as preservatives or sterilants for materials susceptible to microbial contamination.

Such compositions are especially useful in the prevention or treatment of eye infections. Such infections may be caused by bacteria such as, but not limited to, *P. aeruginosa, S. aureus,* and *N. gonorrhoeae*, by fungi such as but not limited to *C. albicans* and *A. fumigatus*, by parasites such as but not limited to *A. castellani*, or by viruses. Applicants have found that significant synergistic effects against such organisms or viruses may be obtained when the ion-channel-forming peptides or proteins are employed in conjunction with a silver-containing composition.

Such compositions may also be effective in killing cysts, spores, or trophozoites of infection-causing organisms. Such organisms include, but are not limited to *Acanthamoeba* which forms trophozoites or cysts, *C. albicans*, which forms spores, and *A. fumigatus*, which forms spores as well.

In accordance with a preferred embodiment, the peptide used in conjunction with a toxic cation is a basic (positively charged) polypeptide having at least sixteen amino acids wherein the polypeptide includes at least eight hydrophobic amino acids and at least eight hydrophilic amino acids. Still more particularly, the hydrophobic amino acids are in groups of two adjacent amino acids, and each group of two hydrophobic amino acids is spaced from another group of two hydrophobic amino acids by at least one amino acid other than a hydrophobic amino acid (preferably at least two amino acids) and generally by no greater than four amino acids, and the amino acids between pairs of hydrophobic amino acids may or may not be hydrophilic.

The hydrophilic amino acids are generally also in groups of two adjacent amino acids in which at least one of the two amino acids is a basic hydrophilic amino acid, with such groups of two hydrophilic amino acids being spaced from each other by at least one amino acid other than a hydrophilic amino acid (preferably at least two amino acids) and generally no greater than four amino acids, and the amino acids between pairs of hydrophilic amino acids may or may not be hydrophobic.

In accordance with a particularly preferred embodiment, the polypeptide comprises a chain of at least four groups of amino acids, with each group consisting of four amino acids. Two of the four amino acids in each group are hydrophobic amino acids, and two of the four amino acids in each group are hydrophilic, with at least one of the hydrophilic amino acids in each group being a basic hydrophilic amino acid and the other being a basic or neutral hydrophilic amino acid.

The hydrophobic amino acids may be selected from the class consisting of Ala, Cys, Phe, Gly, Ile, Leu, Met, Val, Trp, and Tyr. The neutral hydrophilic amino acids may be selected from the class consisting of Asn, Gln, Ser, and Thr. The basic hydrophilic amino acids may be selected from the class consisting of Lys, Arg, His and ornithine (0).

Each of the groups of four amino acids may be of the sequence ABCD, BCDA, CDAB, or DABC, wherein A and B are each hydrophobic amino acids and may be the same or different, one of F or D is a basic hydrophilic amino acid, and the other of C or D is a basic or neutral hydrophilic amino acid and may be the same or different. In a preferred embodiment, the polypeptide chain may comprise 5 or 6 groups of this sequence. In each group, each of A, B, C and D may be the same in some or all of the groups or may be different in some or all of the groups.

The polypeptide chain preferably has at least 20 amino acids, and no greater than 50 amino acids. It is to be understood, however, that the polypeptide does not have to consist entirely of the groups described above. The polypeptide may have amino acids extending from either or both ends of the noted groups forming the polypeptide chain and/or there may be amino acids between one or more of the at least four groups and still remain within the scope of the invention.

The groups of amino acids may be repeating groups of amino acids, or the amino acids in the various groups may vary provided that in each group of the at least four groups of amino acids there are two hydrophobic and two hydrophilic amino acids as hereinabove noted.

Thus, in a preferred embodiment, the biologically active polypeptide comprises a chain including at least four groups of amino acids, each containing four amino acids. Two of the four amino acids in each group are hydrophobic, at least one amino acid is basic hydrophilic, and the remaining one is basic or neutral hydrophilic, with the polypeptide chain preferably having at least 20 amino acids but no greater than 50 amino acids.

In one embodiment, each of the at least four groups of amino acids which are in the peptide chain is of the sequence A-B-C-D, B-C-D-A, C-D-A-B or D-A-B-C wherein A and B are hydrophobic amino acids, one of C or D is basic hydrophilic amino acid, and the other of C or D is basic or neutral hydrophilic amino acid. The resulting polypeptide chain, therefore, may have one of the following sequences:

$(X_1)_a(A\text{-}B\text{-}C\text{-}D)_n(Y_1)_b$ $(X_2)(B\text{-}C\text{-}D\text{-}A)_n(Y_2)_b$ $(X_3)_a(C\text{-}D\text{-}A\text{-}B)_n(Y_3)_b$ $(X_4)_a(D\text{-}A\text{-}B\text{-}C)_n(Y_4)_b$ wherein
$X_1$ is D; C-D- or B-C-D-,
$Y_1$ is -A or -A-B or -A-B-C
$X_2$ is A-, D-A- or C-D-A-
$Y_2$ is -B, -B-C or B-C-D
$X_3$ is B-, A-B-, D-A-B-
$Y_3$ is -C, -C-D, -C-D-A
$X_4$ is C-, B-C-, A-B-C-
$Y_4$ is -D, -D-A, -D-A-B
a is o or 1; b is o or 1 and n is at least 4

It is to be understood that the peptide chain may include amino acids between the hereinabove noted groups of four amino acids provided that the spacing between such groups and the charge on the amino acids does not change the characteristics of the peptide chain which provide amphiphilicity and a positive charge and do not adversely affect the folding characteristics of the chain to that which is significantly different from one in which the hereinabove noted group of four amino acids are not spaced from each other.

As representative examples of peptides in accordance with the present invention, there may be mentioned.

Ala—Phe—Ser—Lys—Ala—Phe—Ser—Lys—Ala—Phe—Ser—    I

```
                                                    -continued
Lys—Ala—Phe—Ser—Lys—Ala—Phe—Ser—Lys
Ala—Phe—Ser—Lys—Ala—Phe—Ser—Lys—Ala—Phe—Ser—    II
Lys—Ala—Phe—Ser—Lys—Ala—Phe—Ser—Lys—Ala—Phe—
Ser—Lys.
Phe—Ser—Lys—Ala—Phe—Ser—                         III
Lys—Ala—Phe—Ser—Lys—Ala—
Phe—Ser—Lys—Ala—
Ser—Lys—Ala—Phe—Ser—Lys—Ala—                     IV
Phe—Ser—Lys—Ala—Phe—Ser—Lys—Ala—
Phe—Ser—Lys—Ala—Phe—
                                                 V
Lys—Ala—Phe—Ser—Lys—Ala—Phe—Ser—Lys—Ala—Phe—Ser—
Lys—Ala—Phe—Ser
```

The peptide, may have amino acids extending form either end of the chain. For example, the chains may have a Ser-Lys sequence before the "Ala" end, and/or an Ala-Phe sequence after the "Lys" end. Other amino acid sequences may also be attached to the "Ala" and/or the "lys" end.

Similarly, in any polypeptide chain having at least four groups of amino acids of the sequence as described above, the chain may have, for example, a C-D sequence before the first A-B-C-D group. Also other amino acid sequences may be attached to the "A" and/or the "D" end of one of these polypeptide chains. Also there may be amino acids in the chain which space one or more groups of the hereinabove noted four amino acids from each other.

The peptides may be produced by known techniques and obtained in substantially pure form For example, the peptides may be synthesized on an automatic synthesizer. Journal of American Chemical Society, Vol 85 Pages 2149-54(1963). It is also possible to produce such peptides by genetic engineering techniques.

In accordance with another preferred embodiment, the peptide employed in conjunction with a toxic cation may be a magainin peptide.

A magainin peptide is either a magainin such as magainin I, II or III or an analogue or derivative thereof. The magainin peptides preferably include the following basic peptide structure $X_{12}$ $$R_{11}\text{-}R_{11}\text{-}R_{12}\text{-}R_{13}\text{-}R_{11}\text{-}R_{14}\text{-}R_{12}\text{-}R_{11}\text{-}R_{13}\text{-}R_{12}\text{-}R_{11}\text{-}R_{11}\text{-}R_{11}\text{-}R_{14a}\text{-}(R_{15})_n\text{-}R_{14a}\text{-}R_{14}$$

wherein $R_{11}$ is a hydrophobic amino acid, $R_{12}$ is a basic hydrophilic amino acid; $R_{13}$ is a hydrophobic, neutral hydrophilic, or basic hydrophilic amino acid; $R_{14}$ and $R_{14a}$ are hydrophobic or basic hydrophilic amino acids; $R_{15}$ is glutamic acid or aspartic acid, or a hydrophobic or a basic hydrophilic amino acid, and n is 0 or 1. In a preferred embodiment, $R_{13}$ is a hydrophobic or neutral hydrophilic amino acid, $R_{14a}$ is a hydrophobic amino acid, and $R_{15}$ is glutamic acid or aspartic acid.

Thus, for example, a magainin peptide may include the following structure:

$$-Y_{12}\text{-}X_{12}\text{-}$$

where $X_{12}$ is the hereinabove described basic peptide structure and $Y_{12}$ is (i) $R_{12}$
(ii) $R_{14a}$—$R_{12}$
(iii) $R_{11}$—$R_{14a}$—$R_{12}$
(iv) $R_{14}$—$R_{11}$—$R_{14a}$—$R_{12}$ where $R_{11}$, $R_{12}$, $R_{14}$ and $R_{14a}$ are as previously defined.

A magainin peptide may also have the following structure:

$$-X_{12}\text{-}Z_{12}\text{-}$$

wherein $X_{12}$ is as previously defined and $Z_{12}$ is:
(i) $R_{16}$ where $R_{16}$ is a basic hydrophilic amino acid or asparagine or glutamine.
(ii) $R_{16}$-$R_{17}$ where $R_{17}$ is a neutral hydrophilic amino acid, a hydrophobic amino acid, or a basic hydrophilic amino acid. Preferably, $R_{17}$ is a neutral hydrophilic amino acid.

A magainin peptide may also have the following structure:

$$(Y_{12})_a\text{-}X_{12}\text{-}(Z_{12})_b$$

where $X_{12}$, $Y_{12}$ and $Z_{12}$ are as previously defined and a is 0 or 1 and b is 0 or 1.

The magainin peptides may also include the following basic peptide structure $X_{13}$:

$$R_{14}\text{-}R_{11}\text{-}R_{14a}\text{-}R_{12}\text{-}R_{11}\text{-}R_{11}\text{-}R_{12}\text{-}R_{13}\text{-}R_{11}\text{-}R_{14}\text{-}R_{12}\text{-}R_{11}\text{-}R_{11}\text{-}R_{12}\text{-},$$

wherein $R_{11}$, $R_{12}$, $R_{13}$, $R_{14}$, and $R_{14a}$ are amino acids as hereinabove described.

The magainin peptide may also include the following structure $X_{13}$-$Z_{13}$; wherein $X_{13}$ is the hereinabove described basic peptide structure and $Z_{13}$ is $$(R_{11n}\text{-}(R_{11n}\text{-}(R_{11})_n\text{-}(R_{14a})_n\text{-}(R_{15})_n\text{-}(R_{14a})_n\text{-}(R_{14})_n\text{-}(R_{16})_n\text{-}(R_{17})_n$$

wherein $R_{11}$, $R_{14}$, $R_{14a}$, $R_{15}$, $R_{16}$, and $R_{17}$ are as hereinabove described, and n is 0 or 1, and each n may be the same or different.

The magainin peptides generally include at least fourteen amino acids and may include up to forty amino acids. A magainin peptide preferably has 22 or 23 amino acids. Accordingly, the hereinabove described basic peptide structures of a magainin peptide may include additional amino acids at the amino end or at the carboxyl end, or at both ends.

As representative examples of such magainin peptides, there may be mentioned peptides having the following primary sequence (expressed as a single letter code) as well as appropriate analogues and derivatives thereof:

| | |
|---|---|
| (NH$_2$) GIGKFLHSAGKFGKAFVGEIMKS(OH) or (NH$_2$) (Magainin I) | (a) |
| (NH$_2$) GIGKFLHSAKKFGKAFVGEIMNS(OH) or (NH$_2$) (Magainin II) | (b) |
| (NH$_2$) GIGKFLHSAKKFGKAFVGEIMN(OH) or (NH$_2$) (Magainin III) | (c) |

The following are examples of peptide derivatives or analogs of the basic structure:

| | |
|---|---|
| (NH$_2$) IGKFLHSAKKFGKAFVGEIMNS(OH) or (NH$_2$) | (d) |
| (NH$_2$) GKFLHSAKKFGKAFVGEIMNS(OH) or (NH$_2$) | (e) |
| (NH$_2$) KFLHSAKKFGKAFVGEIMNS(OH) or (NH$_2$) | (f) |

Magainin peptides are described in *Proc. Natl. Acad Sci.* Vol. 84 pp. 5449-53 (August, 1987). The term "magainin peptides" as used herein refers to the basic magainin structure as well as derivatives and analogs thereof, including but not limited to the representative derivatives or analogs.

In accordance with a further embodiment, the peptide employed in conjunction with a toxic cation may be a PGLa peptide or an XPF peptide.

A PGLa peptide is either PGLa or an analogue or derivative thereof. The PGLa peptides preferably include the following basic peptide structure $X_{14}$:

$$-R_{11}-R_{17}-R_{12}-R_{11}-R_{14}-R_{14}-R_{11}-$$
$$R_{11}-R_{14}-R_{12}-R_{11}-R_{11}-R_{12}-E_{11}-$$
$$R_{11}-R_{11}-E_{12}-$$

where $r_{11}$, $R_{12}$, $R_{14}$, and $R_{17}$ are as previously defined.

The PGLa peptides generally include at least seventeen amino acids and may include as many as forty amino acids. Accordingly, the hereinabove described basic peptide structure for a PGLa peptide may include additional amino acids at the amino end or at the carboxyl end or at both the amino and carboxyl end.

Thus, for example, a PGLa peptide may have the following structure:

$$-Y_{14}-X_{14}-$$

where
$X_{14}$ is as previously defined and
$Y_{14}$ is
  (i) $r_{11}$;
  (ii) $R_{14}-R_{11}$
where $R_{11}$ and $R_{14}$ are as previously defined.

For example, a PGLa peptide may also have the following structure:

$$-X_{14}-Z_{14}-$$

where $X_{14}$ is as previously defined; and $Z_{14}$ is:
  (i) $R_{11}$; or
  (ii) $R_{11}-R_{11}$
where $R_{11}$ is as previously defined.

A PGLa peptide may also have the following structure:

$$(Y_{14})_a-X_{14}-(Z_{14})_b$$

where $X_{14}$; $Y_{14}$ and $z_{14}$ are as previously defined, a is 0 or 1 and b is 0 or 1.

An XPF peptide is either XPF or an analogue or derivative thereof. The XPF peptides preferably include the following basic peptide structure $X_{16}$:

$$R_{11}-R_{17}-R_{12}-R_{11}-R_{14}-R_{18}-R_{17}-$$
$$R_{11}-R_{14}-R_{12}-R_{11}-R_{11}-R_{12}-$$
$$R_{11}-R_{11}-R_{11}-R_{12}-(R_{15})_n-R_{11},$$

wherein $R_{11}$, $R_{12}$, $R_{14}$, $R_{15}$ and $R_{17}$ are as previously defined and $R_{18}$ is glutamine or asparagine or a basic hydrophilic, or hydrophobic amino acid and, n is 0 or 1.

The XPF peptides generally include at least nineteen amino acids and may include up to forty amino acids. Accordingly, the hereinabove described basic peptide structure of XPF may include additional amino acids at the amino end, or at the carboxyl end or at both the amino and carboxyl ends.

Thus, for example, an XPF peptide may include the following structure:

$$-Y_{16}-X_{16}-$$

where $X_{16}$ is as previously defined and $Y_{16}$ is
  (i) $R_{11}$ or
  (ii) $R_{14}-R_{11}$
where $R_{11}$ and $R_{14}$ are as previously defined.

An XPF peptide may include the following structure:

$$-X_{16}-Z_{16}-$$

where $X_{16}$ is as previously defined and $Z_{16}$ is (i) $R_{11}$; or
  (ii) $R_{11}-R_{18}$; or
  (iii) $R_{11}-R_{18}-$Proline; or
  (iv) $R_{11}-R_{18}-$Proline$-R_{12}$ An XPF peptide may also have the following structure:

$$(Y_{16})_a-X_{16}-(Z_{16})_b$$

where $x_{16}$, $Y_{16}$ and $Z_{16}$ are as previously defined: a is 0 or 1 and b is 0 or 1.

Preferred are XPF or PGLa peptides, which are characterized by the following primary amino acid sequence (single letter amino acid code):

PGLa : GMASKAGAIAGKIAKVALKAL (NH$_2$)

XPF : GWASKIGQTLGKIAKVGLKELIQPK

A review of XPF and PGLa can be found in Hoffman et al, *EMBO J.* 2:711-714, 1983; Andreu et al, *J. Biochem.* 149:531-535, 1985; Gibson et al *J. Biol. Chem.* 261:5341-5349, 1986; and Giovannini et al, *Biochem J.* 243:113-120, 1987.

In accordance with yet another embodiment, the peptide employed in conjunction with a toxic cation may be a CPF peptide or appropriate analogue or derviative thereof.

CPF peptides as well as analogues and derivatives thereof are herein sometimes referred to collectively as CPF peptides.

The CPF peptide is preferably one which includes the following peptide structure $X_{30}$:

$$-R_{21}-R_{21}-R_{22}-R_{22}-R_{21}-R_{21}-R_{23}-R_{21}--$$
$$-R_{21}-R_{21}-R_{23}-R_{21}-R_{21}-R_{24}-R_{25}-R_{21}-$$

wherein
$R_{21}$ is a hydrophobic amino acid;
$R_{22}$ is a hydrophobic amino acid or a basic hydrophilic amino acid;
$R_{23}$ is a basic hydrophilic amino acid; and
$R_{24}$ is a hydrophobic or neutral hydrophilic amino acid; and
$R_{25}$ is a basic or neutral hydrophilic amino acid.

The hereinabove basic structure is hereinafter symbolically indicated as $x_{30}$.

The hydrophobic amino acids are Ala, Cys, Phe, Gly, Ile, Leu, Met, Val, Trp, and Tyr.

The neutral hydrophilic amino acids are Asn, Gln, Ser, and Thr.

The basic hydrophilic amino acids are Lys, Arg, His and ornithine.

The CPF peptide may include only the hereinabove noted amino acids or may include additional amino acids at the amino end or carboxyl end or both the amino and carboxyl end. In general, the peptide does not include more than 40 amino acids.

The CPF peptides including the above basic peptide structure may have from 1 to 4 additional amino acids at the amino end. Accordingly, such preferred peptides may be represented by the structural formula:

$$Y_{30}\text{-}X_{30}\text{-}$$

wherein $X_{30}$ is the hereinabove described basic peptide structure and $Y_{30}$ is (i) $R_{25}$—, or
(ii) $R_{22}$—$R_{25}$; or
(iii) $R_{21}$—$R_{22}$—$R_{25}$; or
(iv) $R_{22}$—$R_{21}$—$R_{22}$—$R_{25}$; preferably
Glycine —$R_{21}$—$R_{22}$—$R_{25}$— wherein $R_{21}$, $R_{22}$, and $R_{25}$ are as previously defined.

The carboxyl end of the basic peptide structure may also have additional amino acids which may range from 1 to 13 additional amino acids.

In a preferred embodiment, the basic structure may have from 1 to 7 additional amino acids at the carboxyl end, which may be represented as follows:

$$\text{-}X_{30}\text{-}Z_{30}$$

wherein $X_{30}$ is the hereinabove defined basic peptide structure and $Z_{30}$ is (i) $R_{21}$—,
(ii) $R_{21}$—$R_{21}$—;
(iii) $R_{21}$—$R_{21}$—$R_{24}$;
(iv) $R_{21}$—$R_{21}$—$R_{24}$—$R_{24}$;
(v) $R_{21}$—$R_{21}$—$R_{24}$—$R_{24}$—$R_{26}$;
(vi) $R_{21}$—$R_{21}$—$R_{24}$—$R_{24}$—$R_{26}$—Gln; or
(vii) $R_{21}$—$R_{21}$—$R_{24}$—$R_{24}$—$R_{26}$—Gln—Gln, wherein $R_{21}$ and $R_{24}$ are as previously defined, and $R_{26}$ is proline or a hydrophobic amino acid.

Preferred peptides may be represented by the following structural formula:

$$(Y_{30})_a\text{-}X_{30}\text{-}(Z_{30})_b$$

wherein $X_{30}$, $Y_{30}$ and $Z_{30}$ are as previously defined and a is 0 or 1 and b is 0 or 1.

Representative examples of CPF peptides which are useful in the present invention some of which have been described in the literature and comprise the following sequences (single letter amino acid code):

| | |
|---|---|
| GFGSFLGLALKAALKIGANALGGAPQQ | (1) |
| GLASFLGKALKAGLKIGAHLLGGAPQQ | (2) |
| GLASLLGKALKAGLKIGTHFLGGAPQQ | (3) |
| GLASLLGKALKATLKIGTHFLGGAPQQ | (4) |
| GFASFLGKALKAALKIGANMLGGTPQQ | (5) |
| GFGSFLGKALKAALKIGANALGGAPQQ | (7) |
| GFGSFLGKALKAALKIGANALGGSPQQ | (7) |
| GFASFLGKALKAALKIGANLLGGTPQQ | (8) |

A review of the CPF peptides can be found in Richter, K., Egger, R., and Kreil (1986) J. Biol. Chem. 261, 3676–3680; Wakabayashi, T. Kato, H., and Tachibaba, S. (1985) Nucleic Acids Research 13, 1817–1828; Gibson, B.W., Poulter, L., Williams, D.H., and Maggio, J.E. (1986) J. Biol. Chem. 261, 5341–5349.

CPF peptides which may be employed in the present invention are represented by the following (single letter amino acid code):

G12S3LG4ALKA5LKIG678LGG9(10)QQ

Where:
1 = F, L
2 = G, A
3 = F, L
4 = K, L
5 = A, G, T
6 = A, T
7 = H, N
8 = A, M, F, L
9 = A, S, T
10 = P, L The numbered amino acids may be employed as described in any combination to provide either a basic CPF peptide structure or an analogue or derivative. The term CPF peptide includes the basic peptide structure as well as analogs or derivatives thereof.

In accordance with still another embodiment, the biologically active peptide may include the following basic structure $X_{40}$:

$[R_{41}\text{-}R_{42}\text{-}R_{42}\text{-}R_{43}\text{-}R_{41}\text{-}R_{42}\text{-}R_{42}]_n$, wherein $R_{41}$ is a basic hydrophilic amino acid, $R_{42}$ is a hydrophobic amino acid, $R_{43}$ is a neutral hydrophilic or hydrophobic amino acid, and n is from 2 to 5.

In one embodiment, all of the amino acid residues are D-amino acid residues. Thus, in a preferred embodiment, each of the amino acid residues are D-amino acid residues or L-amino acid residues.

In one embodiment, such peptide may include the following structure:

$Y_{40}\text{-}X_{40}$, wherein $X_{40}$ is as hereinabove described, and $Y_{40}$ is:

(i) $R_{42}$;
(ii) $R_{42}$—$R_{42}$;
(iii) $R_{41}$—$R_{42}$—$R_{42}$;
(iv) $R_{43}$—$R_{41}$—$R_{42}$—$R_{42}$;
(v) $R_{42}$—$R_{43}$—$R_{41}$—$R_{42}$—$R_{42}$; or
(vi) $R_{42}$—$R_{42}$—$R_{43}$—$R_{41}$—$R_{42}$—$R_{42}$, wherein $R_{41}$, $R_{42}$, and $R_{43}$ are as hereinabove described.

In accordance with another embodiment, such peptide may include the following structure:

$X_{40}\text{-}Z_{40}$, wherein $X_{40}$ is as hereinabove described, and $Z_{40}$ is:

(i) $R_{41}$;
(ii) $R_{41}$—$R_{42}$;
(iii) $R_{41}$—$R_{42}$—$R_{42}$;
(iv) $R_{41}$—$R_{42}$—$R_{42}$—$R_{43}$;
(v) $R_{41}$—$R_{42}$—$R_{42}$—$R_{43}$—$R_{41}$; or
(vi) $R_{41}$—$R_{42}$—$R_{42}$—$R_{43}$—$R_{41}$—$R_{42}$.

In accordance another embodiment, such peptide may include the following structure:

$(Y_{40})_a\text{-}X_{40}\text{-}(Z_{40})_b$, wherein Y and Z are as previously defined, a is 0 or 1, and b is 0 or 1.

In one embodiment, n is 3, and most preferably the peptide is of the following structure as indicated by the single letter amino acid code:

$[\text{KIAGKIA}]_3$.

In another embodiment, n is 2, and the peptide preferably is of the following structure as indicated by the single letter amino acid code:

KIA(KIAGKIA)$_2$KIAG.

In accordance with yet another embodiment, the biologically active amphiphilic peptide may be a biologically active amphiphilic peptide including the following basic structure $X_{50}$:

$R_{41}$-$R_{42}$-$R_{42}$-$R_{43}$-$R_{41}$-$R_{42}$-$R_{42}$-$R_{41}$-$R_{42}$-$R_{42}$-$R_{42}$-$R_{41}$-$R_{42}$-$R_{42}$, wherein $R_{41}$, $R_{42}$ and $R_{43}$ are as hereinabove described.

In one embodiment, all of the amino acid residues are D-amino acid residues. Thus, in a preferred embodiment, each of the amino acid residues in the peptide are D-amino acid residues or L-amino acid residues.

In accordance with one embodiment, such peptide may include the following structure:

$Y_{50}$-$X_{50}$, wherein $X_{50}$ is as hereinabove described, and $Y_{50}$ is:

(i) $R_{42}$;
(ii) $R_{42}$—$R_{42}$;
(iii) $R_{41}$—$R_{42}$—$R_{42}$;
(iv) $R_{43}$—$R_{41}$—$R_{42}$—$R_{42}$;
(v) $R_{42}$—$R_{43}$—$R_{41}$—$R_{42}$—$R_{42}$;
(vi) $R_{42}$—$R_{42}$—$R_{43}$—$R_{41}$—$R_{42}$—$R_{42}$, or
(vii) $R_{41}$—$R_{42}$—$R_{42}$—$R_{43}$—$R_{41}$—$R_{42}$—$R_{42}$, wherein $R_{41}$, $R_{42}$ and $R_{43}$ are as hereinabove described.

In accordance with another embodiment, such peptide may include the following structure:

$X_{50}$-$Z_{50}$, wherein $X_{50}$ is as hereinabove described and $Z_{50}$ is:

(i) $R_{41}$;
(ii) $R_{41}$—$R_{42}$;
(iii) $R_{41}$—$R_{42}$—$R_{42}$;
(iv) $R_{41}$—$R_{42}$—$R_{42}$—$R_{43}$;
(v) $R_{41}$—$R_{42}$—$R_{42}$—$R_{43}$—$R_{41}$;
(vi) $R_{41}$—$R_{42}$—$R_{42}$—$R_{43}$—$R_{41}$—$R_{42}$; or
(vii) $R_{41}$—$R_{42}$—$R_{42}$—$R_{43}$—$R_{41}$—$R_{42}$—$R_{42}$, wherein $R_{41}$, $R_{42}$ and $R_{43}$ are as hereinabove described.

In accordance with yet another embodiment the peptide may include the following structure:

$(Y_{50})a$-$X_{50}$-$(Z_{50})b$, wherein X and Y are as previously defined, a is 0 or 1, and b is 0 or 1. In one embodiment, the peptide is of the following structural formula as indicated by the single letter amino acid code:

LKASKAGKIAGKIAKVALKAL.

In another embodiment, the peptide is of the following structural formula as indicated by the single letter amino acid code:

KIAGKIAKIAGOIAKIAGKIA.

In still another embodiment, the peptide employed in conjunction with a toxic cation is a cecropin. The cecropins and analogs and derivatives thereof are described in Ann. Rev. Microbiol 1987 Vol,. 41 pages 103-26, in particular p. 108 and Christensen at al PNAS Vol. 85 p. 5072-76, which are hereby incorporated by reference.

The term cecropins includes the basic structure as well as analogues and derivatives.

In yet another embodiment, the peptide employed in conjunction with the toxic cation is a sarcotoxin. The sarcotoxins and analogs and derivatives thereof are described in Molecular Entomology pages 369-78 in particular p. 375 Alan R. Liss Inc. (1987), which is hereby incorporated by reference.

The term sarcotoxin includes the basic materials as well as analogues and derivatives.

In another embodiment, an ion channel-forming protein may be used in conjunction with a toxic cation. Ion channel-forming proteins which may be employed include defensins, also known as human neutrophil antimicrobial peptides (HNP), major basic protein (MBP) of eosinophils, bactericidal permeability-increasing protein (BPI), and a pore-forming cytotoxin called variously perforin, cytolysin, or pore-forming protein. Defensins are described in Selsted, et al., *J. Clin. Invest.*, Vol. 76, pgs. 1436-1439 (1985). MBP proteins are described in Wasmoen, et al., *J. Biol. Chem.*, Vol. 263, pgs 12559-12563. (1988). BPI proteins are described in Ooi, et al, *J. Biol. Chem.*, Vol. 262, pgs. 14891-14894 (1987). Perforin is described in Henkart, et al., *J. Exp. Med.*, 160: 75 (1984), and in Podack, et al., *J. Exp. Med.*, 160:695 (1984). The above articles are hereby incoroporated by reference.

The term ion channel-forming proteins includes the basic structures of the ion-forming proteins as well as analogues and derivatives.

The present invention will be further described with respect to the following examples, however, the scope of the invention is not to be limited thereby.

EXAMPLE 1

Approximately $1-5 \times 10^5$ colony forming units (CFUs) of *P. aeruginosa* strain 27853, dispersed in 100 $\mu$l of Trypticase soy broth (TSB), were added to each test well. B13-33 peptide was added in increasing concentrations from 0.25 to 256 $\mu$g/ml in the absence of or presence of silver nitrate. Silver nitrate was also added in increasing concentrations from 0.25 to 256 $\mu$g/ml in the absence or presence of B13-33 peptide. B13-33 peptide is of the following structure:

GIGKFLKKAKKFGKAFVKIMKK

The following peptide combinations were tested for Minimal Inhibitory Concentration (MIC) of the B13-33 peptide:

|   | MIC ($\mu$g/ml) |
|---|---|
| 1. B13-33 peptide alone | 4-16 |
| 2. B13-33 peptide plus 5 $\mu$g/ml silver nitrate | <0.03 |

The following combinations were tested for the MIC of silver nitrate:

|   | MIC ($\mu$g/ml) |
|---|---|
| 1. Silver nitrate alone | 4-8 |
| 2. Silver nitrate plus 1.6 $\mu$g/ml B13-33 peptide | 2-8 |
| 3. Silver nitrate plus 5 $\mu$g/ml B13-33 peptide | <0.25 |

As can be seen, in the absence of silver nitrate, the MIC of B13-33 peptide against *P. aeruginosa* strain 27835 was from 4-16 $\mu$g/ml. In the presence of 5 $\mu$g/ml of silver nitrate, the MIC against the same organism fell to less than 0.03 μg/ml.

In the absence of B13-33 peptide, the MIC of silver nitrate against *P. aeruginosa* was 2-8 μg/ml. When 5 μg/ml of B13-33 peptide was added, the MIC fell to less than 0.25 μg/ml.

EXAMPLE 2

Approximately $1-5\times10^5$ CFUs of *P. aeruginosa* strain 27853 dispersed in 100 μl of TSB were added to each test well. Either Peptide 1 or Peptide 2 was added in increasing concentrations from 0.25 to 256 μg/ml in the absence of or in the presence of silver nitrate.

Peptide 1 is of the following structure:

[KIAGKIA]₃

Peptide 2 is of the following structure:

KIAGKIAKIAGOIAKIAGKIA.

The following combinations of Peptide 1 or Peptide 2, with or without silve nitrate, were tested for Minimal Inhibitory Concentration (MIC) of Peptide 1 or Peptide 2:

|  | MIC (μg/ml) |
|---|---|
| 1. Peptide 1 alone | 16-32 |
| 2. Silver nitrate alone | 8 |
| 3. Peptide 1 plus 5 μg/ml silver nitrate | <0.03 |
| 4. Peptide 2 alone | 16 |
| 5. Peptide 2 plus 5 μg/ml silver nitrate | <0.03 |

EXAMPLE 3

Approximately $1-5\times10^5$ CFUs of a clinical isolate of a methicillin resistant *S. aureus* (MSRA), dispersed in 100 μl of TSB were added to each test well. Either B13-33, Peptide 1, or Peptide 2 was added in increasing concentrations from 0.25 to 256 μg/ml in the absence of or the presence of silver nitrate. The MIC of each peptide alone, and of silver nitrate alone was determined. The MIC of each peptide when 5 μg/ml and/or 10 μg/ml of silver nitrate was added was determined as well. The MIC of the various peptides and combinations of peptides and silver nitrate are listed below.

|  | MIC (μg/ml) |
|---|---|
| 1. B13-33 alone | 4 |
| 2. Silver nitrate alone | 16 |
| 3. B13-33 plus 5 μg/ml silver nitrate | 1 |
| 4. B13-33 plus 10 μg/ml silver nitrate | <0.03 |
| 5. Peptide 1 alone | 8 |
| 6. Peptide 1 plus 10 μg/ml silver nitrate | 1 |
| 7. Peptide 2 alone | 8 |
| 8. Peptide 2 plus 10 μg/ml silver nitrate | 1 |

EXAMPLE 4

Approximately $1-5\times10^5$ CFUs of *P. eruginosa* strain 27853 dispersed in 100 μl of TSB were added to each test well. Cecropin A-D was added in increasing amounts from 0.25 μg/ml to 256 μg/ml in the absence of or in the presence of silver nitrate.

Cecropin A-D is of the following structure:

KWKLFKKIEKVGQRVRDAVISAGPAVAT-VAQATALAK.

The following combinations of Cecropin A-D with or without silver nitrate, were tested for Minimal Inhibitory Concentration (MIC) of Cecropin A-D;

|  | MIC (μg/ml) |
|---|---|
| 1. Cecropin A-D alone | 16 |
| 2. Silver nitrate alone | 8 |
| 3. Cecropin A-D plus 3 μg/ml silver nitrate | <0.25 |

EXAMPLE 5

Approximately $1-5\times10^5$ CFUs of *P. aeruginosa* strain 27853 dispersed in 100 μl of TSB were added to each test well. Magainin II (amide-terminated) was added in increasing amounts from 0.25 to 256 μg/ml in the absence of or in the presence of silver nitrate. The following combinations of Magainin II, with or without silver nitrate, were tested for Minimal Inhibitory Concentration (MIC) of Magainin II:

|  | MIC (μg/ml) |
|---|---|
| 1. Magainin II alone | 256 |
| 2. Silver nitrate alone | 8 |
| 3. Magainin II plus 1 μg/ml silver nitrate | 32 |
| 4. Magainin II plus 2 μg/ml silver nitrate | 16 |
| 5. Magainin II plus 3 μg/ml silver nitrate | 8 |
| 6. Magainin II plus 4 μg/ml silver nitrate | <0.03 |

EXAMPLE 6

Approximately $1-5\times10^5$ CFUs of *P. aeruginosa* strain 107 which was gentamicin resistant, dispersed in 100 μl of TSB were added to each test well. Magainin II (amide-terminated) was added in increasing amounts from 0.25 to 256 μg/ml in the absence of or in the presence of silver nitrate. The following combinations of Magainin II, with or without silver nitrate, were tested for Minimum Inhibitory Concentration (MIC) of Magainin II:

|  | MIC (μg/ml) |
|---|---|
| 1. Magainin II alone | 256 |
| 2. Silver nitrate alone | 8 |
| 3. Magainin II plus 1 μg/ml silver nitrate | 32 |
| 4. Magainin II plus 2 μg/ml silver nitrate | 16 |
| 5. Magainin II plus 3 μg/ml silver nitrate | 16 |
| 6. Magainin II plus 4 μg/ml silver nitrate | 4 |
| 7. Magainin II plus 5 μg/ml silver nitrate | <0.03 |

The peptide or protein and toxic cation, as hereinabove described, may be employed for treating a wide variety of hosts. In accordance with a preferred embodiment, a host is an animal, and such animal may be a human or non-human animal. The peptide or protein and the toxic cation may be employed together in a single composition, or in separate compositions. Moreover, the toxic cation and the peptide or protein may be delivered or administered in different forms, for example, the toxic cation may be administered topically, while the peptide or protein may be administered by IV or IP.

The peptide or protein and/or toxic cation may be employed in a wide variety of pharmaceutical compositions in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule, or the like. The peptide or protein and/or toxic cation may also be used in combination with adjuvants, protease inhibitors, or compatible drugs where such a combination is seen to be desirable or advantageous in controlling infection caused by harmful microorganisms including protozoa, viruses, parasites and the like.

The peptide(s) or protein of the present invention may be administered to a host; in particular an animal, in an effective antibiotic and/or anti-viral and/or anti-microbial and/or anti-parasitic amount in conjunction with a toxic cation for potentiating the activity of the peptide or protein.

As representative examples of administering the peptide or protein and toxic cation for topical or local administration, the peptide could be administered in an amount of up to about 1% weight to weight and the toxic cation delivered in an amount of about 50 mM (about 0.1%). Alternatively, the toxic cation could be administered topically in conjunction with systemic administration of the peptide and/or protein. For example, the peptide or protein may be administered IV or IP to achieve a serum dose of 100 micrograms per milliliter (10 milligrams per kilogram) in conjunction with a topical dose of toxic cation of from about 4 μg/ml to about 100 μg/ml.

Numerous modifications and variations of the present invention are possible in light of the above teachings and, therefore, within the scope of the appended claims, the invention may be practiced otherwise than as particularly described.

What is claimed is:

1. A process for inhibiting growth of a target cell or virus in a host, comprising:
   administering to a host at least one biologically active amphiphilic peptide and/or biologically active protein, said peptide or protein being an ion channel-forming peptide or protein; and a toxic cation, said components being administered in a combined amount effective to inhibit growth of a target cell or virus in a host.

2. The process of claim 1 wherein the peptide is a magainin peptide.

3. The process of claim 1 wherein the peptide is a cecropin.

4. The process of claim 1 wherein the peptide is a sarcotoxin.

5. The process of claim 1 wherein the peptide is a XPF peptide.

6. The process of claim 1 wherein the peptide is a PGLa peptide.

7. The process of claim 1 wherein the peptide is a CPF peptide.

8. The process of claim 1 wherein the peptide includes the following basic structure $X_{40}$:

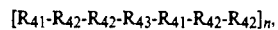

$[R_{41}\text{-}R_{42}\text{-}R_{42}\text{-}R_{43}\text{-}R_{41}\text{-}R_{42}\text{-}R_{42}]_n$, wherein $R_{41}$ is a basic hydrophilic amino acid, $R_{42}$ is a hydrophobic amino acid, $R_{43}$ is a neutral hydrophilic or hydrophobic amino acid, and n is from 2 to 5.

9. The process of claim 1 wherein the peptide includes the following basic structure $X_{50}$:

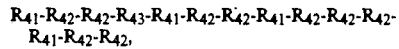

$R_{41}\text{-}R_{42}\text{-}R_{42}\text{-}R_{43}\text{-}R_{41}\text{-}R_{42}\text{-}R_{42}\text{-}R_{41}\text{-}R_{42}\text{-}R_{42}\text{-}R_{42}\text{-}R_{41}\text{-}R_{42}\text{-}R_{42}$, wherein $R_{41}$ is a basic hydrophilic amino acid, $R_{42}$ is a hydrophobic amino acid, and $R_{43}$ is a neutral hydrophilic or hydrophobic amino acid.

10. The process of claim 1 wherein said toxic cation is selected from the class consisting of silver cations, zinc cations, mercury cations, arsenic cations, copper cations, platinum cations, antimony cations, gold cations, thallium cations, nickel cations, selenium cations, bismuth cations, and cadmium cations.

11. The process of claim 10 wherein said toxic cation is a silver cation.

12. The process of claim 11 wherein said silver cation is employed as part of a silver-containing compound.

13. The process of claim 12 wherein said silver-containing compound is silver nitrate.

14. The process of claim 1 wherein the peptide and toxic cation are administered separately.

15. The process of claim 1 wherein the peptide is administered topically.

16. The process of claim 1 wherein the toxic cation is administered topically.

17. The process of claim 1 wherein the peptide and toxic cation are both administered topically.

18. The process of claim 1 wherein the peptide and the toxic cation are administered in effective antibiotic amounts.

19. A composition, comprising:
   (a) at least one biologically active amphiphilic peptide and/or biologically active protein, said peptide or protein being an ion channel-forming peptide or protein;
   (b) a toxic cation; and
   (c) an acceptable pharmaceutical carrier, wherein said components (a) and (b) are present in a combined amount effective to inhibit growth of a target cell or virus in a host.

20. The composition of claim 19 wherein the peptide is a magainin peptide.

21. The composition of claim 19 wherein the peptide is a cecropin.

22. The composition of claim 19 wherein the peptide is a sarcotoxin.

23. The composition of claim 19 wherein the peptide is a XPF peptide.

24. The composition of claim 19 wherein the peptide is a PGLa peptide.

25. The composition of claim 19 wherein the peptide is a CPF peptide.

26. The composition of claim 19 wherein the peptide includes the following basic structure $X_{40}$:

$[R_{41}\text{-}R_{42}\text{-}R_{42}\text{-}R_{43}\text{-}R_{41}\text{-}R_{42}\text{-}R_{42}]_n$ wherein R$_{41}$ is a basic hydrophilic amino acid, R$_{42}$ is a hydrophobic amino acid, R$_{43}$ is a neutral hydrophilic or hydrophobic amino acid, and n is from 2 to 5.

27. The composition of claim 19 wherein the peptide includes the following basic structure X$_{50}$:

R$_{41}$-R$_{42}$-R$_{42}$-R$_{43}$-R$_{41}$-R$_{42}$-R$_{42}$-R$_{41}$-R$_{42}$-R$_{42}$-R$_{42}$-R$_{41}$-R$_{42}$-R$_{42}$, wherein R$_{41}$ is a basic hydrophilic amino acid, R$_{42}$ is a hydrophobic amino acid and R$_{43}$ is a neutral hydrophilic or hydrophobic amino acid.

28. The composition of claim 19 wherein said toxic cation is selected from the class consisting of silver cations, zinc cations, mercury cations, arsenic cations, copper cations, platinum cations, antimony cations, gold cations, thallium cations, nickel cations, selenium cations, bismuth cations, and cadmium cations.

29. The composition of claim 28 wherein said toxic cation is a silver cation.

30. A method of treating or preventing infections of the eye in a host, comprising administering to said host at least one biologically active peptide and/or biologically active protein, said peptide or protein being an ion channel-forming peptide or protein, and a toxic cation, said components being administered in a combined amount effective to inhibit growth of a target cell or virus in a host.

31. The method of claim 30 wherein said toxic cation is selected from the class consisting of silver cations, zinc cations, mercury cations, arsenic cations, copper cations, platinum cations, antimony cations, gold cations, thallium cations, nickel cations, selenium cations, bismuth cations, and cadmium cations.

32. The method of claim 31 wherein said toxic cation is a silver cation.

33. The method of claim 32 wherein said silver cation is employed as part of a silver-containing compound.

34. The method of claim 33 wherein the silver-containing compound is silver nitrate.

35. The method of claim 30 wherein the peptide is administered topically.

36. The method of claim 30 wherein the toxic cation is administered topically.

37. The method of claim 30 wherein the peptide and the toxic cation are both administered topically.

38. A method of treating or preventing skin infections in a host, comprising:
administering to a host at least one biologically active peptide and/or biologically active protein, said peptide or protein being an ion channel-forming peptide or ion channel-forming protein, and a toxic cation, said components being administered in a combined amount effective to inhibit growth of a target cell or virus in a host.

39. The method of claim 38 wherein said toxic cation is selected from the class consisting of silver cations, zinc cations, mercury cations, arsenic cations, copper cations, platinum cations, antimony cations, gold cations, thallium cations, nickel cations, selenium cations, bismuth cations, and cadmium cations.

40. The method of claim 39 wherein said toxic cation is a silver cation.

41. The method of claim 40 wherein said silver cation is employed as part of a silver-containing compound.

42. The process of claim 41 wherein the silver-containing compound is silver nitrate.

43. A method of treating or preventing burn infections in a host, comprising:
administering to a host at least one biologically active amphiphillic peptide and/or biologically active protein, said peptide or protein being an ion channel-forming peptide or ion channel-forming protein, and a toxic cation, said components being administered in a combined amount effective to inhibit growth of a target cell or virus in a host.

44. The method of claim 43 wherein said toxic cation is selected from the class consisting of silver cations, zinc cations, mercury cations, arsenic cations, copper cations, platinum cations, antimony cations, gold cations, thallium cations, nickel cations, selenium cations, bismuth cations, and cadmium cations.

45. The method of claim 44 wherein said toxic cation is a silver cation.

46. The method of claim 45 wherein said silver cation is employed as part of a silver-containing compound.

47. The method of claim 46 wherein the silver-containing compound is silver nitrate.

48. The process of claim 1 wherein the peptide has the following structural formula:

GIGKFLKKAKKFGKAFVKIMKK.

49. The process of claim 8 wherein the peptide has the following structural formula:

[KIAGKIA[$_3$

50. The process of claim 9 wherein the peptide has the following structural formula:

KIAGKIAKIAGOIAKIAGKIA.

51. The process of claim 2 wherein the magainin peptide is Magainin II.

52. The process of claim 3 wherein the cecropin is Cecropin A—D.

53. The composition of claim 19 wherein the peptide has the following structural formula:

GIGKFLKKAKKFGKAFVKIMKK.

54. The composition of claim 19 wherein the peptide has the following structural formula:

[KIAGKIA]$_3$

55. The composition of claim 19 wherein the peptide has the following structural formula:

KIAGKIAKIAGOIAKIAGKIA.

56. The composition of claim 20 wherein the magainin peptide is Magainin II.

57. The composition of claim 21 wherein the cecropin is Cecropin A-D.

58. A process for inhibiting growth of a target cell or a virus in a host, comprising:
administering to a host (a) at least one biologically active amphiphilic peptide selected from the group consisting of:
(i) a magainin peptide;
(ii) a cecropin;
(iii) a sarcotoxin;
(iv) an XPF peptide;

(v) a PGLa peptide;
(vi) a CPF peptide;
(vii) a peptide including the following basic structure $X_{40}$:

$[R_{41}\text{-}R_{42}\text{-}R_{42}\text{-}R_{43}\text{-}R_{41}\text{-}R_{42}\text{-}R_{42}]_n$, wherein $R_{41}$ is a basic hydrophilic amino acid, $R_{42}$ is a hydrophobic amino acid, and $R_{43}$ is a neutral hydrophilic amino acid, and n is from 2 to 5;

(viii) a peptide which includes the following basic structure $X_{50}$:

$R_{41}\text{-}R_{42}\text{-}R_{42}\text{-}R_{43}\text{-}R_{41}\text{-}R_{42}\text{-}R_{42}\text{-}R_{41}\text{-}R_{42}\text{-}R_{42}\text{-}R_{42}\text{-}R_{41}\text{-}R_{42}\text{-}R_{42}$, wherein $R_{41}$ is a basic hydrophilic amino acid, $R_{42}$ is a hydrophobic amino acid, and $R_{43}$ is a neutral hydrophilic or hydrophobic amino acid;

(ix) a basic polypeptide having at least sixteen amino acids, wherein said basic polypeptide includes at least eight hydrophobic amino acids and at least eight hydrophilic amino acids; and (b) a toxic cation, said components (a) and (b) being administered in a combined amount effective to inhibit growth of a target cell in a host.

59. The process of claim 58 wherein the peptide is a magainin peptide.

60. The process of claim 59 wherein the magainin peptide is Magainin II.

61. The process of claim 59 wherein the magainin peptide has the following structural formula:

GIGKFLKKAKKFGKAFVKIMKK

62. The process of claim 58 wherein the peptide is a cecropin.

63. The process of claim 62 wherein the cecropin is Cecropin A-D.

64. The process of claim 58 wherein the peptide includes the following basic structure $X_{40}$:

$[R_{41}\text{-}R_{42}\text{-}R_{42}\text{-}R_{43}\text{-}R_{41}\text{-}R_{42}\text{-}R_{42}]_n$, wherein $R_{41}$ is a basic hydrophilic amino acid, $R_{42}$ is a hydrophobic amino acid, $R_{43}$ is a neutral hydrophilic or hydrophobic amino acid, and n is from 2 to 5.

65. The process of claim 64 wherein the peptide has the following structural formula:

[KIAGKIA]$_3$.

66. The process of claim 58 wherein the peptide includes the following basic structure $X_{50}$:

$R_{41}\text{-}R_{42}\text{-}R_{42}\text{-}R_{43}\text{-}R_{41}\text{-}R_{42}\text{-}R_{42}\text{-}R_{41}\text{-}R_{42}\text{-}R_{42}\text{-}R_{42}\text{-}R_{41}\text{-}R_{42}\text{-}R_{42}$, wherein $R_{41}$ is a basic hydrophilic amino acid, $R_{42}$ is a hydrophobic amino acid, and $R_{43}$ is a neutral hydrophilic or hydrophobic amino acid.

67. The process of claim 66 wherein said peptide has the following structural formula:

KIAGKIAKIAGOIAKIAGKIA

68. A composition comprising:

(a) at least one biologically active amphiphilic peptide selected from the class consisting of:
(i) a magainin peptide;
(ii) a cecropin;
(iii) a sarcotoxin;
(iv) an XPF peptide;
(v) a PGLa peptide;
(vi) a CPF peptide;
(vii) a peptide including the following basic structure $x_{40}$:

$[R_{41}\text{-}R_{42}\text{-}R_{42}\text{-}R_{43}\text{-}R_{41}\text{-}R_{42}\text{-}R_{42}]_n$, wherein $R_{41}$ is a basic hydrophilic amino acid, $R_{42}$ is a hydrophobic amino acid, $R_{43}$ is a neutral hydrophilic amino acid or hydrophobic amino acid, and n is from 2 to 5; and (viii) a peptide including the following basic structure $X_{50}$:

$R_{41}\text{-}R_{42}\text{-}R_{42}\text{-}R_{43}\text{-}R_{41}\text{-}R_{42}\text{-}R_{42}\text{-}R_{41}\text{-}R_{42}\text{-}R_{42}\text{-}R_{42}\text{-}R_{41}\text{-}R_{42}\text{-}R_{42}$, wherein $R_{41}$ is a basic hydrophilic amino acid, $R_{42}$ is a hydrophobic amino acid, and $R_{43}$ is a neutral hydrophilic or hydrophobic amino acid;

(ix) a basic polypeptide having at least sixteen amino acids, wherein said basic polypeptide includes at least eight hydrophobic amino acids and at least eight hydrophilic amino acids;

(b) a toxic cation; and (c) an acceptable pharmaceutical carrier, wherein said components (a) and (b) are present in a combined effective amount to inhibit growth of a target cell or virus in a host.

69. The composition of claim 68 wherein the peptide is a magainin peptide.

70. The composition of claim 69 wherein the magainin peptide is Magainin II.

71. The composition of claim 69 wherein the magainin peptide has the following structural formula:

GIGKFLKKAKKFGKAFVKIMKK

72. The composition of claim 68 wherein the peptide is a cecropin.

73. The composition of claim 72 wherein the cecropin is Cecropin A-D.

74. The composition of claim 68 wherein the peptide includes the following basic structure $X_{40}$:

$[R_{41}\text{-}R_{42}\text{-}R_{42}\text{-}R_{43}\text{-}R_{41}\text{-}R_{42}\text{-}R_{42}]_n$, wherein $R_{41}$ is a basic hydrophilic amino acid, $R_{42}$ is a hydrophobic amino acid, $R_{43}$ is a neutral hdyrophilic amino acid or hydrophobic amino acid, and n is from 2 to 5.

75. The composition of claim 74 wherein the peptide has the following structural formula:

[KIAGKIA]$_3$

76. The composition of claim 68 wherein the peptide includes the following basic structure $X_{50}$:

$R_{41}\text{-}R_{42}\text{-}R_{42}\text{-}R_{43}\text{-}R_{41}\text{-}R_{42}\text{-}R_{42}\text{-}R_{41}\text{-}R_{42}\text{-}R_{42}\text{-}R_{42}\text{-}R_{41}\text{-}R_{42}\text{-}R_{42}$, wherein $R_{41}$ is a basic hydrophobic amino acid, $R_{42}$ is a hydrophobic amino acid, and $R_{43}$ is a neutral hydrophilic or hydrophobic amino acid.

77. The composition of claim 76 wherein said peptide has the following structural formula:

KIAGKIAKIAGOIAKIAGKIA

78. The method of claim 38 wherein the peptide or protein is administered topically.

79. The method of claim 38 wherein the toxic cation is administered topically.

80. The method of claim 38 wherein the peptide or protein and toxic cation both are administered topically.

81. The method of claim 43 wherein the peptide or protein is administered topically.

82. The method of claim 43 wherein the toxic cation is administered topically.

83. The method of claim 43 wherein the peptide or protein and toxic cation both are administered topically.

84. The method of claim 58 wherein said toxic cation is selected from the class consisting of silver cations, zinc cations, mercury cations, arsenic cations, copper cations, platinum cations, antimony cations, gold cations, thallium cations, nickel cations, selenium cations, bismuth cations, and cadmium cations.

85. The method of claim 84 wherein said toxic cation is a silver cation.

86. The method of claim 85 wherein said silver cation is employed as part of a silver-containing compound.

87. The method of claim 86 wherein the silver-containing compound is silver nitrate.

88. The method of claim 58 wherein the peptide or protein is administered topically.

89. The method of claim 58 wherein the toxic cation is administered topically.

90. The method of claim 58 wherein the peptide or protein and the toxic cation both are administered topically.

91. The composition of claim 68 wherein said toxic cation is selected from the class consisting of silver cations, zinc cations, mercury cations, arsenic cations, copper cations, platinum cations, antimony cations, gold cations, thallium cations, nickel cations, selenium cations, bismuth cations, and cadmium cations.

92. The composition of claim 91 wherein said toxic cation is a silver cation.

93. The method of claim 92 wherein said silver cation is employed as part of a silver-containing compound.

94. The method of claim 93 wherein the silver-containing compound is silver nitrate.

* * * * *